United States Patent [19]

Wolf et al.

[11] Patent Number: 4,592,910

[45] Date of Patent: * Jun. 3, 1986

[54] PREPARATION FOR DEACTIVATING VIRUSES AND PROCESS FOR PRODUCING SAME

[75] Inventors: Erich Wolf, Overath; Andreas Lembke, Eutin-Sielbeck; Rolf Deininger, Cologne, all of Fed. Rep. of Germany

[73] Assignee: Chimicasa GmbH, Chur, Switzerland

[*] Notice: The portion of the term of this patent subsequent to Sep. 6, 2001 has been disclaimed.

[21] Appl. No.: 398,705

[22] Filed: Jul. 15, 1982

Related U.S. Application Data

[60] Division of Ser. No. 184,135, Sep. 4, 1980, Pat. No. 4,402,950, which is a continuation of Ser. No. 5,764, Jan. 23, 1979, Pat. No.

[30] Foreign Application Priority Data

Jan. 27, 1978 [LU] Luxembourg ............................. 78955

[51] Int. Cl.$^4$ ............................................... A61K 35/78

[52] U.S. Cl. .................................. 424/195.1; 514/962
[58] Field of Search .............................. 424/195, 195.1

[56] References Cited

U.S. PATENT DOCUMENTS 3,595,975 7/1971 Gauvreau ............................. 424/263

OTHER PUBLICATIONS

Chem. Abst. 59:14406a 1963.

Primary Examiner—Jerome D. Goldberg
Assistant Examiner—John W. Rollins
Attorney, Agent, or Firm—Peter K. Kontler

[57] ABSTRACT

The invention relates to a process and a preparation for deactivating viruses inside living human and animal organisms by application of a terpene obtainable from aromatic plants by steam distillation. The terpenes cited are: black pepper oil, cinnamon flower oil, cardamon oil, linallyl acetate, cinnamic aldehyde, safrol, carvon and cis/trans citral.

19 Claims, No Drawings

PREPARATION FOR DEACTIVATING VIRUSES AND PROCESS FOR PRODUCING SAME

This application is a division, of application Ser. No. 184,135, filed Sept. 4, 1980 now U.S. Pat. No. 4,402,950 which is a continuation of Ser. No. 005,764, filed Jan. 23, 1979, now abandoned.

The invention relates to a process and a preparation for deactivating viruses inside living human and animal organisms. During use thereof, cell damage and other harmful side effects in the organisms should be prevented.

The process according to the invention is characterised by the use of a terpene obtainable by steam distillation from aromatic plants, in a daily dose of 5 to 500 mg (mmiligrams), preferably 25 to 100 mg per 50 kg (kilograms) of the weight of the living organism.

These terpenes demonstrate a viricidal activity (i.e. a damaging effect on viruses) in a concentration which is one or more powers of ten lower than the concentration at which these terpenes have toxic effects on living cells. This wide range gives a degree of play in tolerance which is advantageous from the dosage point of view and thus makes it possible to administer these terpenes safely in veterinary and human medicine.

Since these terpenes can be obtained from aromatic plants which have been used for feeding animals and humans for many years and have proved harmless in the doses in question, it is also to be expected that the quantities of terpenes to be used according to the invention will not cause any serious, harmful side effects.

Terpenes or mixtures of terpenes which have proved suitable are those consisting of black pepper oil, cinnamon flower oil, cardamom oil, linallyl acetate, cinnamic aldehyde, safrol, carvon and cis/trans citral, used individually or mixed together.

A pharmaceutical preparation according to the invention, i.e. for deactivating viruses inside living human and animal organisms, is prepared by obtaining one or more of these terpenes by steam distillation from the parts of the aromatic plants where the relevant terpenes are contained and then mixing them into a pharmaceutical carrier substance in a ratio of 1:100 to 20:100.

A pharmaceutical preparation according to the invention, i.e. for deactivating viruses inside living human and animal organisms, consists of one or more of the terpenes listed, mixed into a pharmaceutical carrier substance in a ratio of 1:100 to 20:100.

The terpenes used can be obtained from aromatic plants by steam distillation as follows:
black pepper oil from the peppercorns of Piper nigrum;
cinnamon flower oil from the flowers of Cinnamonum Cassia;
cardamom oil from the seeds of Elctiaria Cardamomum;
linallyl acetate from the flowers of Lavandula;
cinnamic aldehyde from the bark of Cinnamomum ccylanicum;
safrol from the roof of Sassafras;
carvon from the fruit of Carum carvi, and
cis/trans citral from the leaves of Cymbopogon citratus.

Instead of these natural terpenes, identical synthetic terpenes may be used, if available. However, natural terpenes obtained from aromatic plants are preferred.

The activity obtained according to the invention is demonstrated by comparison tests as follows.

Cell cultures were cultivated in various culture vessels under optimal culture conditions from permanent strains of the types "Girardi Heart" (GH), "Flow 12000" (FL), "Intestine 407" (IX) and "Vero Kidney" (VE), so that a layer of cell culture containing about 0.25 mg of cell substance formed on the bottom of the vessels.

A suspension of virus particles of the Adeno Type 6 virus was also added.

For the total of eight terpenes listed in Table I, twenty cell cultures of each type of cell were prepared. The twenty cell cultures of each type of cell were treated with differing amounts of the relevant terpene in the following manner.

The first two cell cultures were given $10^5$ mg of terpene per 10 kg of cell substance. The next two cell cultures were given $10^4$ mg of terpene based on 10 kg of cell substances. The next two cell cultures were given $10^3$ mg of terpene based on 10 kg of cell substance and so on to the last two of these twenty cell cultures, which were given 0.1 mg of terpene per 10 kg of cell substance. Thus, in each case, two similar cell cultures were treated with the same amount of the same terpene. For control purposes, one of these two identical cell cultures was left as it was, whilst the other was inoculated with $5 \times 10^6$ virus particles per 0.25 mg of cell substance, in addition to the virus suspension used. The same procedure was also followed with the other cell cultures and terpenes.

The cell cultures thus treated were left to stand and observed after four days and six days. This observation was carried out by microscopic investigation of the cell culture for cell damage. The damage observed was divided into four stages, as follows:

| | | |
|---|---|---|
| State 0 | means | no damage |
| Stage 1 | means | slackened growth of the cell formations |
| Stage 2 | means | the cells become spherical and detach themselves from the bottom |
| Stage 3 | means | the cell structures are substantically or totally destroyed. |

It was found that the inoculated cell cultures which were protected with a very small amount of terpene reached stage 3 or 2, as the viruses had damaged the cells. The inoculated cell cultures containing a very large amount of terpene also reached stage 3 or 2, as the cells were damaged by the excessive terpene. However, the inoculated cell cultures containing only a moderate amount of terpene were at stage 0, i.e undamaged. Thus, the moderate amount of terpene damaged the viruses sufficiently and protected the cells from viral attack, without the cells being damaged directly by the terpene. The terpene concentrations with which stage 0 and, in some isolated cases, stage 1 were observed in the inoculated cell cultures after four and six days result in sufficient damage to the viruses without damaging the cells, and are given in Table I.

Column 1 of Table I gives the terpene used, the second column gives the treated cell strain, abbreviated as hereinbefore, and the third column gives the amount of terpenes used in mg, based on 10 kg of treated cell substance, for the range of concentrations in which no appreciable cell damage (i.e. stage 0) was observed. This range is the therapeutic range which in each case extends over several powers of ten. Thus, for all the terpenes listed in the Table, the desired viricidal activity occurs at a concentration which is several powers of ten lower than the lowest concentration at which cell damage was observed, i.e. at which the microorganisms to be protected could be damaged.

TABLE I

| Terpene | treated cell substance | range of viricidal concentration at which no cell damage was observed, in mg of terpene per 10 kg of treated cell substance |
|---|---|---|
| black pepper oil | GH | $10^3$ to 0.1 |
| (Oleum Piperis nigri) | FL | 100 to 0.1 |
| | IN | 100 to 1 |
| | VE | 100 to 0.1 |
| Cinnamon flower oil | GH | $10^3$ to 0.1 |
| (Oleum Cassiac flores) | FL | $10^3$ to 0.1 |
| | IN | 100 to 0.1 |
| | VE | 100 to 0.1 |
| Cardamon oil | GH | 100 to 1 |
| (Oleum Cardamoni) | FL | 100 to 1 |
| | IN | 100 to 1 |
| | VE | 100 to 10 |
| Linallyl acetate | GH | 100 to 0.1 |
| | FL | 100 to 1 |
| | IN | 100 to 1 |
| | VE | 100 to 1 |
| cinnamic aldehyde | GH | 100 to 1 |
| | FL | 100 to 1 |
| | IN | 100 to 1 |
| | VE | 100 to 1 |
| sairol | GH | 100 to 1 |
| | FL | 100 to 1 |
| | IN | 100 to 10 |
| | VE | 100 to 1 |
| carvoa | GH | 100 to 1 |
| | FL | 100 to 1 |
| | IN | 100 to 1 |
| | VE | 100 to 1 |
| cis/trans citral | GH | 10 to 1 |
| | FL | 10 to 1 |
| | IN | 100 to 1 |
| | VE | 100 to 1 |

EXAMPLE 1 (Injection solution)

50 g of black pepper oil are dissolved in 2 l (liters) of 1,2-propanediol. The solution is sterilized in the autoclave for 50 minutes at 121° C. (Celsius), then cooled and poured into ampoules in 2 g amounts.

An ampoule contains 50 mg of black pepper oil and contains an average daily dose for an adult weighing 70 kg, for the therapy and proplylaxis of influenza infections. For human and animal patients of other weights, the daily dose must be modified accordingly in proportion to the patient's weight.

The mixing ratio of terpene to 1,2-propanediol in this example is 2.5:100; other mixing ratios for injection solutions are possible, within the range 1:100 to 5:100, but the daily dose of the injection solution must then be adjusted to the different terpene content of the injection solution.

EXAMPLE 2 (Aerosol)

325 g of black pepper oil are dissolved in 631.8 g of other mixed with 1,305.07 g of ethanol. To this solution are added 31.6 g of ester of castor oil fatty acids with ethoxylated glycerol and 210.6 g of capryl/capric acid triglyceride. 2.68 g of this mixture, together with 2.527 g of difluorodichloromethane as the propellant, are packed in a spray can with a capacity of 20 cc (cubic centimeters). The spray can is sealed and comprises a metering valve which releases a specific amount of mixture each time it is actuated, and this mixture is then vaporised as an aerosol under the pressure of the difluorodichloromethane.

Corresponding adjustment and dimensions of the metering valve ensure that, on each application, a single dose containing 6.5 mg of black pepper oil is released.

For the treatment and prevention of influenza infections, the aerosol is sprayed into the mouth or nose and inhaled. A suitable treatment for an adult weighing 70 kg is eight such single doses per day, containing a total of $8 \times 6.5 = 50$ mg of black pepper oil.

The aerosol can also be used to treat areas of the skin affected by virus infections, in which case an area of 50 $cm^2$ (square centimeters) is sprayed with seven spray doses each containing 6.5 mg of black pepper oil.

The mixing ratio of terpene to the aerosol substance is 12:100 in this example; other mixing ratios for the aerosol are possible, in the range from 5:100 to 20:100, but then the daily dose must be adjusted to the modified terpene content of each spray portion.

EXAMPLE 3 (Capsules)

A capsule filling is prepared from a mixture of 12.5 g of black pepper oil and 12.5 g of cinnamon flower oil and 3 g of soya lecithin as the emulsifier. Each capsule contains 28 mg of this filling and is sealed with a capsule shell consisting of 87.5 mg of gelatine and 37.5 mg of glycerol.

For the treatment and prevention of influenza infections, one to four capsules per day are administered orally to an adult patient weighing 70 kg; if more than one capsule is taken, they are spread out over the day.

One capsule contains 25 mg of terpene; however, variations are possible, with a capsule containing from 10 to 50 mg of terpene, but then the daily dose must be adjusted to the modified terpene content.

EXAMPLE 4 (Stick)

1 g of black pepper oil is mixed into a stable carrier composition. The carrier composition consists of 59.84 g of Vaseline album and 39.16 g of paraffin and is thoroughly mixed with the terpene at 70° C. and then poured into a mould to form a stick and hardened by cooling.

For local use, the stick is rubbed on to the skin and distributed so that 1 ml (milliliter) of stick compound-which contains 5 mg of terpene in this example-is distributed over 50 $cm^2$ of skin. This can be repeated 3 times daily.

The mixing ratio of terpene to carrier composition is 1:100 in this example; other mixing ratios are possible, in the range from 1:100 to 5:100.

EXAMPLE 5 (Ointment)

3.2 g of Paraffinum durum and 86.8 g of white Vaseline are heated to 60° C. and stirred. 10 g of cinnamon flower oil are mixed into the warm mixture. The mixture is cooled and can be used as an ointment for local application. About 0.1 ml of ointment-containing about 5 mg of terpene-are spread over 50 $cm^2$ of skin. This can be repeated 8 times a day.

The mixing ratio of terpene to the mixture of Paraffinum durum and white Vaseline is 11:100 in this example, but other mixing ratios for the ointment are also possible, within the range from 5:100 to 20:100.

EXAMPLE 6 (Plaster)

A vapour-proof plaster film is produced from textile material made vapour-proof by coating with plastics on the underside. On the other side (the contact side) the plaster is coated with a plaster compound in a layer 1 mm (millimeter) thick. To prepare the plaster compound, 97 g of lead plaster, 8 g of yellow wax, 9 g of dammar, 10 g of colophony and 1 g of turpentine are mixed together, heated to 100° C. and stirred until the molten compound is no longer foaming. Then 5 g of black pepper oil are mixed in and the plaster compound is then applied to the contact side of the plaster film and hardened by cooling.

The plaster is placed with its contact side next to the skin and left for four hours. It can then be replaced by a new plaster.

The mixing ratio of terpene to plaster compound is 4:100 in this example; however, other mixing ratios are also possible within the range from 1:100 to 10:100.

Using the preparations and treatments given in the examples, viral attacks can be prevented or stopped without causing any cell damage in the treated organism or any other serious side effects.

The examples given are open to modification by using, instead of the terpene mentioned, the some amount of another terpene from Table I or a mixture of several of these terpenes. In all these cases, the viricidal activity can be obtained without having to take into account any undesirable side effects.

We claim:

1. A process for preparing a pharmaceutical composition for deactivating viruses inside living human and animal organisms, comprising the steps of
   deriving a terpene from black pepper oil by steam distillation; and
   admixing said derived terpene in a pharmaceutical carrier in a mixing ratio of terpene to carrier of from about 1:100 to about 20:100.

2. The process of claim 1, wherein said plant is *Piper nigrum*.

3. The process of claim 1, wherein said pharmaceutical carrier is 1,2-propanediol.

4. A pharmaceutical aerosol composition for humans and animals for deactivating viruses, including
   a terpene derived from black pepper oil; and
   an aerosol carrier vehicle in a ratio of between about 5:100 and about 20:100 of terpene to carrier vehicle.

5. The composition of claim 4, wherein said mixing ratio of terpene to carrier vehicle is about 12:100.

6. The composition of claim 4, wherein said carrier vehicle includes ether, ethanol, an ester of a castor oil fatty acid with ethoxylated glycerol, capryl/capric acid triglyceride and difluorodichloromethane.

7. The composition of claim 6, wherein said carrier vehicle includes about 1 part by weight of ether, between about 2 and about 5 parts by weight of ethanol, between about 0.02 and about 0.1 parts by weight of an ester of a castor oil fatty acid with ethoxylated glycerol, between about 0.2 and about 1 part by weight of capryl/capric acid triglyceride and between about 2 and about 6 parts of difluorodichloromethane.

8. The composition of claim 4, wherein the ratio of said black pepper oil to the aerosol carrier vehicle is about 12:100.

9. A pharmaceutical capsule composition for ingestion by humans and animals for deactivating viruses, including a terpene derived from black pepper oil; an emulsifier; and a capsule casing, the weight of said terpene being between about 10 mg and about 50 mg and the weight of said capsule being between about 80 mg and 200 mg.

10. The composition of claim 9, wherein said emmulsifier is soya lecithin.

11. The composition of claim 9, wherein said capsule casing consists of gelatine and glycerol in a ratio of between about 2:1 and about 3:1 by weight.

12. The composition of claim 9, wherein the weight of said terpene is between about 10 mg and about 50 mg and the weight of said capsule is between about 80 and about 200 mg.

13. A stable, spreadable pharmaceutical stick composition for external application by humans and animals for deactivating viruses, including a terpene derived from black pepper oil; and a carrier consisting of vaseline album and paraffin in a ratio of between about 1:1 and about 2:1 by weight, the weight ratio of terpene to carrier being between about 1:100 and about 5:100.

14. The composition of claim 13, wherein said weight ratio is about 1:100.

15. A pharmaceutical ointment composition for external application by humans and animals for deactivating viruses, including a terpene derived from black pepper oil; and an ointment carrier consisting of Paraffinum durum and white vaseline in a weight ratio of between about 1:20 and about 1:35, the weight ratio of terpene to carrier being between about 5:100 and about 20:100.

16. The composition of claim 5, wherein the ratio is about 11:100.

17. A pharmaceutical capsule composition for ingestion by humans and animals for deactivating viruses, including a terpene derived from black pepper oil; an emulsifier; and a capsule casing, the weight of said emulsifier being between about 1 mg and about 8 mg and the weight of said capsule being between about 80 mg and about 200 mg.

18. The composition of claim 17, wherein said emulsifier is soya lecithin.

19. The composition of claim 17, wherein said capsule casing consists of gelatine and glycerol in a ratio of between about 2:1 and about 3:1 by weight.

* * * * *